(12) United States Patent
Dafforn et al.

(10) Patent No.: US 10,989,651 B2
(45) Date of Patent: Apr. 27, 2021

(54) MOLECULAR DETECTION SYSTEM

(71) Applicant: The University of Birmingham, Birmingham (GB)

(72) Inventors: Timothy Dafforn, Warwickshire (GB); Matthew Hicks, West Midlands (GB)

(73) Assignee: The University of Birmingham, Birmingham (GB)

( * ) Notice: Subject to any disclaimer, the term of this patent is extended or adjusted under 35 U.S.C. 154(b) by 383 days.

(21) Appl. No.: 15/314,034

(22) PCT Filed: May 28, 2015

(86) PCT No.: PCT/GB2015/051544
§ 371 (c)(1),
(2) Date: Nov. 25, 2016

(87) PCT Pub. No.: WO2015/181546
PCT Pub. Date: Dec. 3, 2015

(65) Prior Publication Data
US 2017/0191927 A1    Jul. 6, 2017

(30) Foreign Application Priority Data

May 28, 2014 (GB) ..................... 1409426

(51) Int. Cl.
*G01N 21/19* (2006.01)
*G01N 21/05* (2006.01)
(Continued)

(52) U.S. Cl.
CPC ........... *G01N 21/19* (2013.01); *C12Q 1/6825* (2013.01); *G01N 21/05* (2013.01); *G01N 21/21* (2013.01);
(Continued)

(58) Field of Classification Search
CPC ............ C12Q 1/6825; C12Q 2563/107; G01N 21/05; G01N 21/19; G01N 21/21;
(Continued)

(56) References Cited

U.S. PATENT DOCUMENTS

| | | | | |
|---|---|---|---|---|
| 6,159,686 A | * | 12/2000 | Kardos | .................. B82Y 15/00 250/484.2 |
| 2003/0224370 A1 | | 12/2003 | Rassman et al. | |
| 2013/0344508 A1 | * | 12/2013 | Schwartz | ........... G01N 33/5306 435/7.21 |

FOREIGN PATENT DOCUMENTS

| | | | |
|---|---|---|---|
| JP | 2006-343207 A | 12/2006 | |
| JP | 2010-510482 A | 4/2010 | |

(Continued)

OTHER PUBLICATIONS

Morimatsu (2006) Anal Biochem 358:192-198. (Year: 2006).*
(Continued)

*Primary Examiner* — Christopher L Chin
*Assistant Examiner* — Richard Moerschell
(74) *Attorney, Agent, or Firm* — Brooks Kushman P.C.

(57) ABSTRACT

A molecular sensor that utilises dichroism can be used to identify the presence of specific molecules in a substance. The molecular sensor includes a sensor element comprising (i) a scaffold moiety and (ii) one or more receptor molecules for the target molecule attached to the scaffold moiety to form a scaffold/receptor complex, wherein the scaffold/receptor complex is modified to incorporate a chromophore and the modified scaffold/receptor complex has a high aspect ratio.

7 Claims, 5 Drawing Sheets

(51) Int. Cl.
  *G01N 21/21* (2006.01)
  *C12Q 1/6825* (2018.01)
  *G01N 33/569* (2006.01)

(52) U.S. Cl.
  CPC . *G01N 33/56916* (2013.01); *G01N 2201/061* (2013.01); *G01N 2201/0683* (2013.01); *G01N 2333/245* (2013.01); *G01N 2333/255* (2013.01); *G01N 2469/10* (2013.01)

(58) Field of Classification Search
  CPC ..... G01N 2201/061; G01N 2201/0683; G01N 2333/245; G01N 2333/255; G01N 2469/10; G01N 33/56916
  USPC ......................................................... 436/524
  See application file for complete search history.

(56) References Cited

FOREIGN PATENT DOCUMENTS

| | | | |
|---|---|---|---|
| JP | 2003-510609 A1 | 3/2018 | |
| WO | WO2000/040751 A2 | 7/2000 | |
| WO | WO2003/026590 A2 | 4/2003 | |
| WO | WO 2008/059280 * | 5/2008 | ............. G01N 21/19 |
| WO | WO2008/059280 A1 | 5/2008 | |

OTHER PUBLICATIONS

Nafisi J Mol Struct (Year: 2006).*
Japanese Office Action dated Jul. 9, 2019 issued in connection with Japanese Patent Appl. No. 2016-570019.

* cited by examiner

Selective detection of different sensor elements

Figure 5

Internal standard

MOLECULAR DETECTION SYSTEM

FIELD OF THE INVENTION

The present invention relates to a molecular sensor that utilises dichroism to identify the presence of specific molecules in a substance. The invention also relates to a sensor element for use in the sensor.

BACKGROUND TO THE INVENTION

By their nature, organisms contain many complex molecules and molecular assemblies. Some of the most important molecules and assemblies are large and have high aspect ratios (i.e. one axis significantly greater in length than any other). It is known to use an optical apparatus to specifically detect these high aspect ratio molecules. Such an apparatus relies on the way these long molecules interact with polarised light (i.e. light with an electric field established in one direction only).

The phenomenon being exploited in the above apparatus is known as dichroism. The incident light may be either linearly polarised, giving rise to linear dichroism (LD), or circularly polarised, giving rise to circular dichroism (CD). LD is the property exhibited by some molecular structures whereby linearly polarised light is differentially absorbed along two orthogonal axes. CD relates to the difference in absorption of left and right circularly polarised light. A molecule that is capable of selective light absorption is known as a chromophore. Dichroic molecules, i.e. those that exhibit dichroic properties, are a particular type of chromophore. Examples of dichroic materials are certain natural crystals, stretched polymers, and other non-isotropic molecules. Biomolecules contain a wide range of chromophores (including aromatic side chains, nucleotides and peptide backbones).

In order to be able to observe a dichroic effect, it is necessary that the chromophores be aligned, or at least partially aligned, with respect to the incident polarised light beams. This requirement has the advantage of allowing the extraction of data only from aligned molecules in a milieu of unaligned molecules. However, this requirement has, to date, also limited the application of the above technique, primarily, to the study of large molecules with high aspect ratios, since these are easily alignable. A molecule is considered to have a high aspect ratio if one axis is substantially longer than the other. Suitable molecules may be in the shape of a rod, a disc or a cruciform. Some examples of moieties of interest that have been successfully aligned include linear biomolecules in the form of DNA, fibrous proteins and membranes (including membrane proteins) (Marrington R, Small E, Rodger A, Dafforn T R, Addinall S G, "FtsZ fiber bundling is triggered by a conformational change in bound GTP" J Biol Chem 2004; 279(47):48821-48829; Dafforn T R, Rajendra J, Halsall D J, Serpell L C, Rodger A, "Protein fiber linear dichroism for structure determination and kinetics in a low-volume, low-wavelength couvette flow cell" Biophys J 2004; 86(1 Pt 1):404-410; Dafforn T R, Rodger A, "Linear dichroism of biomolecules: which way is up?" Curr Opin Struct Biol 2004; 14(5):541-546; Halsall D J, Rodger A, Dafforn T R, "Linear dichroism for the detection of single base pair mutations" Chem Commun (Camb) 2001(23):2410-2411).

A particularly convenient method for aligning such molecules is to create a solution including the molecules and then to flow the solution. Due to the elongate nature of the molecules, alignment arises as a result of shear forces generated by the flow, making the sample suitable for exhibiting the effect of linear dichroism.

In a known apparatus, once the molecules of interest have been aligned, linearly polarised light is directed through the solution from a direction substantially perpendicular to the axes of the aligned molecules. Absorption of light occurs within a molecule because, at a particular wavelength, the electric field of radiation urges the electrons in the molecule in a particular direction. When several molecules are similarly aligned, the electrons in each are all characterised by the same preferred net displacement direction. LD is a measure of the difference of absorbance of the incident light between two orthogonal polarisations. Varying the wavelength of the incident light and detecting the light emerging from the sample, allows a spectrum to be obtained which illustrates the absorbance of the sample with respect to wavelength.

An LD spectrum of a molecule provides information on the chromophores that are present including the orientation of the chromophores (and hence molecular conformation) and the orientation of the chromophores with respect to the axes of polarization. This information is important in understanding the structure of the molecule. Note that LD is a measurement of a sample's bulk property. The strength of the absorbance can be used to quantify the number of target molecules that are present in the sample. In addition, since LD is extremely sensitive to changes in alignment, an anomaly in the structure of a molecule may be detected. For example, LD can detect the distortion caused by a single mismatched hydrogen bond in a 1300 bp (base pair) fragment of DNA.

Furthermore, LD is extremely sensitive to the formation of a complex since the binding of an aligned molecule to a second molecule has the following two measurable effects.
1) The shape of the aligning moiety is altered and this results in its alignment also being altered, which leads to a change in the observed LD spectrum.
2) The second molecule itself becomes aligned by virtue of its attachment to the aligned molecule. This leads to the generation of an LD signal for the previously unaligned chromophores of the second molecule. Thus, information on the structure of the complex can be obtained.

Both of the above effects result in detectable phenomena that can be used to detect the formation of complexes. Not only can structural information be gleamed regarding the nature of the complex but the affinity of the interaction can also be determined.

Unfortunately, most molecules do not have a high aspect ratio and instead have shapes more closely related to spheres, with aspect ratios of less than approximately 5:1. In order to align these molecules it is necessary to link the target molecule to a receptor that itself has a high aspect ratio. This method of alignment has been achieved and has been applied to studies of ligands (e.g. cisplatin) that bind to naturally alignable receptors (e.g. DNA). However, this method is also limited in its application since only those molecules that bind to naturally alignable receptors can be studied.

WO 2008/059280 addressed the above issue by providing a molecular sensor in which the sensor element comprised a scaffold moiety with a high aspect ratio having a receptor moiety attached thereto. The use of an alignable scaffold moiety as a substrate for the attachment of a receptor moiety meant that neither the receptor moiety itself nor the target molecule required inherent alignment properties. As well as being able to identify the aligned molecules through the resulting dichroic spectrum, the sensor can be used to quantify the aligned molecules and to detect the presence of molecular anomalies such as mismatches. The binding properties of the receptor moiety and target molecule may also be studied using the sensor. The inherent nature of dichroic molecules means that the sensor is extremely sensitive.

The present invention represents a further development of the sensor disclosed in WO 2008/059280 and aims to expand the application of dichroic analysis.

SUMMARY OF THE INVENTION

According to a first aspect of the present invention there is provided a molecular sensor comprising:
 a flow path configured for flowing a solution potentially containing a target molecule;
 a source of polarized light;
 a detector arranged to receive light from the source after it has passed through the flowpath; and
 a plurality of sensor elements disposed in use in the flow path, each sensor element comprising (i) a scaffold moiety and (ii) one or more receptor molecules for the target molecule attached to the scaffold moiety to form a scaffold/receptor complex, wherein the scaffold/receptor complex is modified to incorporate a chromophore and the modified scaffold/receptor complex has a high aspect ratio.

It will be understood that what is meant by the scaffold/receptor complex being modified is that a specific chromophore is incorporated to tune the exhibited dichroism of the sensor element to a desired wavelength.

As used herein a high aspect ratio relates to an aspect ratio greater than 5:1, greater than 10:1, greater than 20:1, greater than 50:1, greater than 75:1 and in some embodiments greater than 100:1.

The scaffold moiety may have a high aspect ratio. It will be understood that it is crucial that the modified scaffold/receptor complex align and provide the absorbance necessary for dichroism. However the scaffold moiety, receptor moiety or indeed the scaffold/receptor complex themselves need not themselves absorb or align. The chromophore itself could be the alignable moiety (i.e. have a high aspect ratio and be aligned under flow). Alternatively, the combination of scaffold and chromophore could create a moiety that is alignable, for example by changing the aspect ratio and/or rigidity of the scaffold.

Examples of suitable scaffold moieties include:—
 synthetic polymers,
 carbon nanotubes,
 biomolecular fibres
 crystals
 inorganic particles, e.g. metal fragments
 synthetic biology constructs
 mixtures of liquids of different polarities (so as to create phase separation and subsequent alignment of regions of the minor phase)

As used herein a biomolecular fibre is any biomolecule having the required high aspect ratio and which is alignable under flow conditions. Examples of biomolecular fibres include lipid vesicles, filamentous bacteriophage and polymers such as amino acid polymers (i.e. polypeptides or proteins) and nucleic acid polymers (i.e. RNA or DNA).

In some embodiments the modified scaffold/receptor complex exhibits dichroism in the visible spectrum (i.e. 400 to 700 nm).

In certain embodiments the biomolecular fibre is a filamentous bacteriophage, such as M13, f1, fd, Ike and N1.

The chromophore is attached to the scaffold/receptor complex in such a way that it is not in free exchange with the other scaffold/receptor complex. In certain embodiments the attachment is by one or more covalent bonds (which may be to either the scaffold or receptor moieties).

Examples of suitable chromophores include those in Table 1 below.

TABLE 1

| Class of Chromophore | Examples (non-exhaustive list) |
| --- | --- |
| AlexaFluor(AF) | AF405, AF488, AF555, AF610, AF647, AF700. |
| Spiro compounds | Fluorescamine, |
| Xanthones | e.g. Fluoresceins (Fluorescein-isothiocyanate, N-hydroxysuccinimide-Fluorescein Rhodamines (Rhodamine-isothiocyanate, Tetra-methyl-rhodamine-isothiocyanate) |
| Benzopyrones | Coumarin |
| DNA intercalators | Ethidium bromide |
| Others | Eosin-5-maleimide, NBD-chloride, BHQ-10-succinimidyl ester, lanthanide complexes, quantum dots, Dansyl, Pyrene |

It will be appreciated that the receptor needs to have sufficient specificity for the target such that it will distinguish the target from other non-target molecules. In some embodiments, the receptor is a peptide or protein, for example an affimer.

In some embodiments, the receptor comprises an antibody or an antibody fragment capable of specifically binding to a target molecule.

In a first series of embodiments each sensor element comprises the same scaffold/receptor complex modified with the same receptor molecule(s).

In a second series of embodiments, the sensor comprises a plurality of distinct groups of sensor elements, the groups having the same scaffold moieties but different chromophores and receptor molecules for different target molecules, such that the dichroic absorbance of each group of sensor elements is at a different wavelength to that of the other groups and each group detects a different target molecule.

It will be understood that said second series of embodiments permits multiplexing, i.e. a determination of multiple target molecules in a single assay, because the dichroic absorbance for each specific target molecule will be at a different wavelength.

The flowpath is conveniently provided by a couette cell.

The invention also resides in a sensor element comprising (i) a scaffold moiety and (ii) one or more receptor molecules for the target molecule attached to the scaffold moiety to form a scaffold/receptor complex, wherein the scaffold/receptor complex is modified to incorporate a chromophore and the modified scaffold/receptor complex has a high aspect ratio.

The invention further resides in a kit of sensor elements, the kit comprising a plurality of distinct groups of sensor elements, each sensor element comprising a scaffold moiety and a receptor for a target molecule forming a scaffold/receptor complex, wherein the scaffold/receptor complexes of each group are modified with a different chromophore and the receptor molecules are for different target molecules, and wherein all the modified scaffold/receptor complexes have a high aspect ratio and the dichroic absorbance of each group of sensor elements is at a different wavelength to that of the other groups.

The kit may comprise for example two, three, four or five groups of sensor elements.

According to a second aspect of the invention there is provided a method for detecting a plurality of different target molecules in a flowing solution comprising providing in a flow path a plurality of distinct groups of sensor elements, each sensor element comprising a scaffold moiety and a receptor for a target molecule forming a scaffold/receptor complex, wherein the scaffold/receptor complexes of each group are modified with a different chromophore and the receptor molecules of each group are for different target molecules, and wherein the modified scaffold/receptor complexes have a high aspect ratio and the dichroic absorbance of each group of sensor elements is at a different wavelength to that of the other groups; flowing a solution potentially containing a target molecule along the flow path; passing light through the flow path; and detecting the light after it has passed through the flow path; to produce a linear dichroism spectrum of the solution.

It will be understood that the light incident on the flow-path may be linearly polarised (e.g. using a source of polarised light or appropriately filtering the light before it reaches the flowpath), or the incident light may be unpolarised with the use of a detector capable of detecting the polarisation of light in two orthogonal orientations after it has passed through the flowpath.

BRIEF DESCRIPTION OF THE DRAWINGS

The invention will be further described by way of example only with reference to the accompanying drawings in which.

DETAILED DESCRIPTION OF CERTAIN EMBODIMENTS

Figure 1:
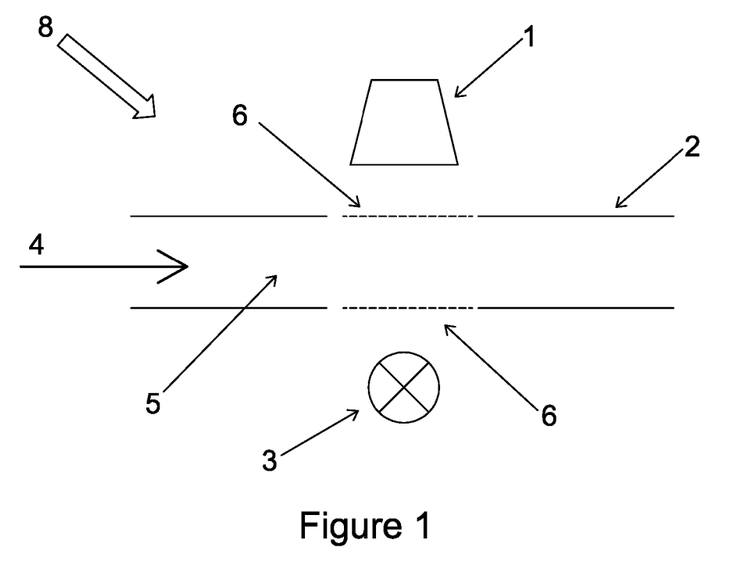
FIG. 1 is a schematic of a sensor in accordance with the present invention.

With reference to FIG. 1, there is illustrated a molecular sensor 8 according to the present invention. The sensor 8 comprises a flow path in the form of an elongate pipe 2 that is mostly made from plastics material and is opaque. The central portion of the pipe 2 is configured as an observation window 6 and is made from a material that is transparent to the wavelength of light employed. In this particular example, the observation window 6 is made from glass quartz, which is transparent to visible light. Thus, in this example the observation window 6 is configured to allow light in the wavelength range of approximately 400 nm to 700 nm to pass therethrough. Adjacent one side of the observation window 6 is a light source 3. The light source 3 is configured to emit two orthogonal linearly polarised beams of light through the observation window 6 and thereby through the flow path 5. Disposed opposite to the light source 3, on the other side of the observation window 6 and the flow path 5, is a detector 1. The detector 1 is configured to detect the light beams emitted by the light source 3 once they have passed through the observation window 6 and the flow path 5.

In use, a liquid solution containing a plurality of sensor elements each comprising a scaffold moiety bound to one or more receptor molecules for a target molecule in the form of a scaffold/receptor complex, complex modified with a chromophore such that the modified scaffold/receptor complex has a high aspect ratio is mixed with a sample to be analysed. The solution, which may include the target molecules of interest, is flowed through the pipe 2 in the direction indicated by arrow 4 in FIG. 1. The effects of this are shown schematically in FIG. 2 for a system in which there are two groups of sensor elements each distinguished from the other by having different chromophores and receptor moieties for different target molecules.

Figure 2:
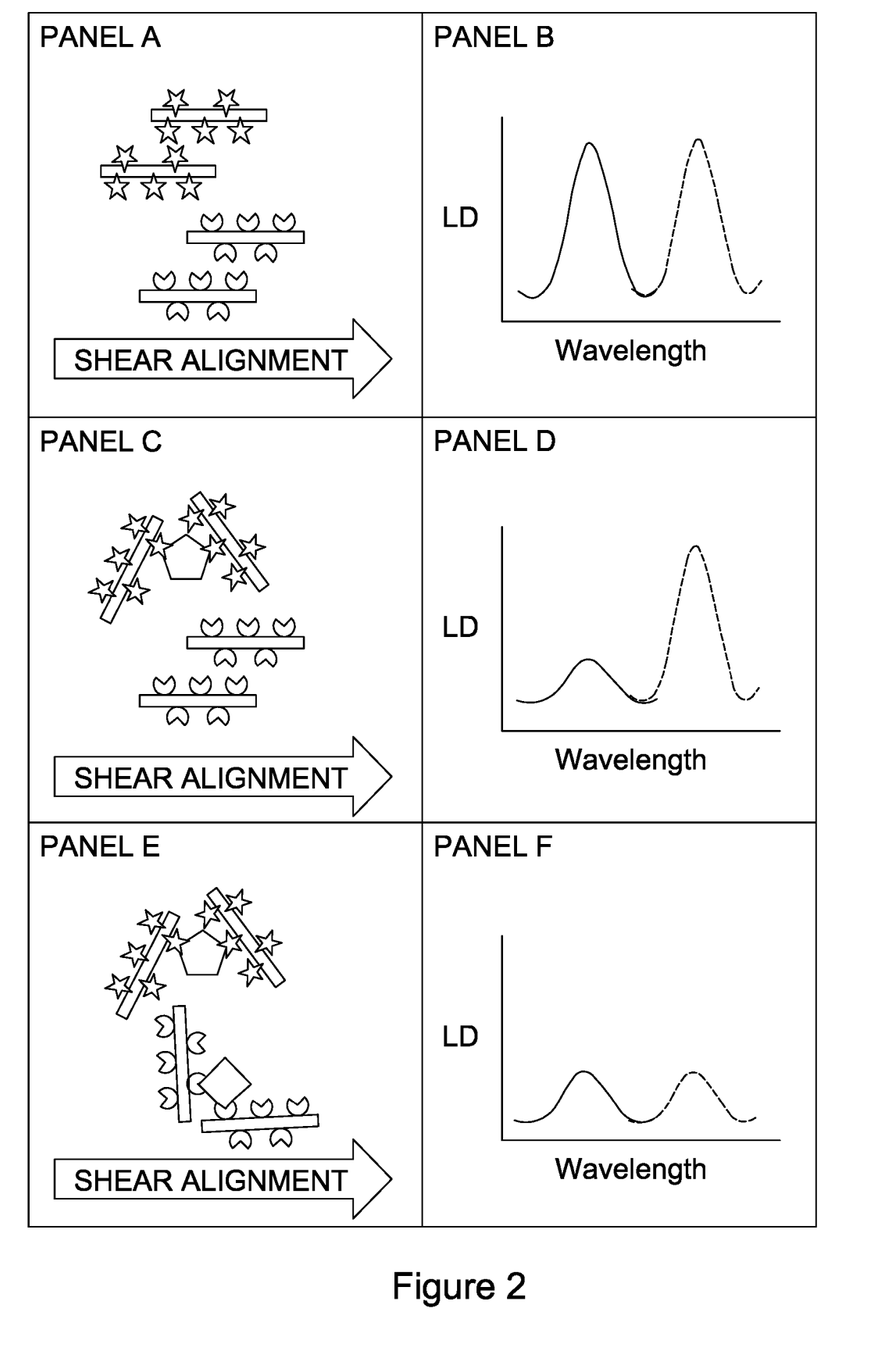
FIG. 2 is a representation of the method of the present invention in operation with different target molecules present and the associated LD spectra.

Referring to FIG. 2 Panel A, a first sensor element has a scaffold moiety, covalently linked to a first chromophore and a first receptor moiety designed to bind a first target molecule. A second sensor element comprises the same scaffold moiety, covalently linked to a second chromophore and a second receptor moiety designed to bind a second target molecule. The chromophores are chosen such that the LD spectra they produce are distinguishable.

Under flow conditions the sensor elements are aligned and in the absence of target molecules two distinct peaks are observed in the LD spectrum (Panel B).

When the first target molecule is present (the second target molecule being absent), the first receptors bind to it and the alignment of the first sensor elements is disrupted, thereby reducing the peak in the LD spectrum (Panel D). It will be understood that the relative heights of the peaks in panels B and D is a quantitative measure of how much of the first target molecule is present. The alignment of the second sensor elements is unaffected and so the associated peak in the LD spectrum is unchanged. It will be understood that a similar situation will arise if the second target molecule is present and the first target molecule is absent, except the alignment of the second sensor elements is disrupted and its associated peak in the LD spectrum is reduced (not shown).

Where both first and second target molecules are present, alignment of both the first and second sensor elements is disrupted (Panel E) leading to a reduction in both associated peaks in the LD spectrum (Panel F). Although the peaks are shown as being reduced by the same amount, it will of course be understood that the heights of the peaks will vary independently based on the quantities of the first and second target molecules in the sample under test.

In order to achieve an LD signal from a chromophore it must be attached to a scaffold/receptor complex ideally by a covalent bond or alternatively by another method that ensures that the chromophore is not in free exchange with the solution or other scaffolds. The chromophore must also be arranged on the scaffold/receptor complex such that it is non-isotropic or ordered with respect to the scaffold/receptor complex. Linear dichroism results from chromophores being aligned in an ordered fashion with respect to a beam of linear polarised light. This order could be introduced either by:

1) Steric hindrance between the chromophore and the scaffold/receptor complex and/or other chromophores
2) Attachment of a single chromophore to the scaffold/receptor complex by multiple bonds (covalent or non-covalent)

In the example below chromophores are covalently linked to bacteriophage (an alignable scaffold) to induce an LD signal from the chromophore. The chromophores were attached to the Lysine residues on the g8p coat protein of bacteriophage M13. The chromophores attached include those in table 1 above. For each dye the labelling efficiency ranged from 100-30% and in each case an LD spectrum was observed for each dye at a wavelength corresponding to the absorbance wavelength of the dye.

Although in this example, amine group of lysine residues were used as the coupling site for the chromophores a number of other methods could be used for such a scaffold. These include coupling via the amine groups of the amino terminus of any protein, the sulfidryl of cysteine residues and carboxylate of aspartate and glutamate residues as well as the carboxy terminus of any protein, but any linking chemistry that links the chromophore to the scaffold could be used. For other non-proteinaceous scaffolds e.g. DNA, membrane vesicles, carbon nanotubes and ordered arrays of small molecules, other linkage chemistries may be employed which might also include the incorporation of the chromophore into a precursor which is subsequently assembled into an alignable scaffold.

Once a number of alignable scaffold/receptor complexes have been produced containing different chromophores these reagents can either be combined in an assay that allows multiple assay targets to be detected and/or embed positive and negative control reactions into the assay.

Method
Conjugation of Pathogen Recognition Antibody and Chromophore on to Bacteriophage M13
This method is carried out using the following steps:
1) Derivatisation of the antibody (Ab) with Succinimidyl-4-(N-maleimidomethyl) cyclohexane-1-carboxylate (SMCC) to convert accessible amine groups to maleimide groups.
2) Mixing the M13 and antibody together to conjugate the two moieties to give M13-Ab.
3) Derivatisation of the dye molecule (BHQ10-succinimide) with amino-ethyl-maleimide to convert the succinimide group to a maleimide group to give BHQ10-maleimide.
4) Mixing the M13-Ab with BHQ10-maleimide to give M13-Ab-BHQ10.

Figure 3:
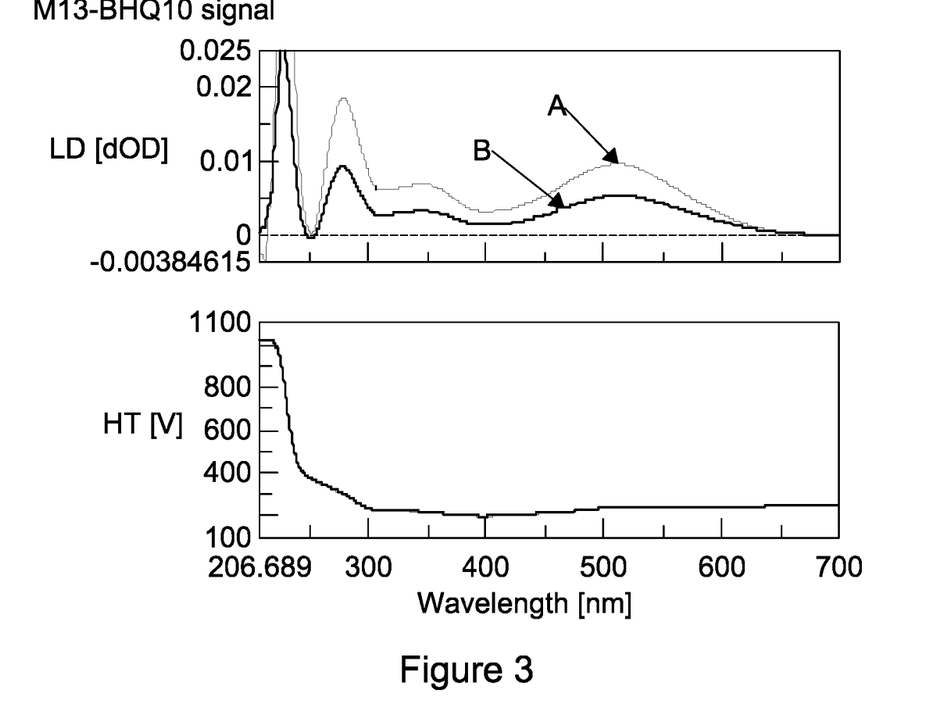
FIG. 3 shows LD spectra resulting from M13 labelled with a dye (BHQ10) and an antibody to *E. coli* O157 in the absence and presence of *E. coli* O157 (the target), FIG. 4 demonstrates the measurement of multiple M13-dye sensor elements in the same sample.

The resulting sensor element gives rise to an LD signal corresponding to the wavelength of the absorbance of BHQ10 (FIG. 3 thin line). Addition of the target analyte (in this case E. coli O157) results in interaction of the antibody on the sensor element interacting with the O-antigen of the E. coli with subsequent disruption in the alignment of the sensor element and a change (decrease in this case) in the LD signal (FIG. 3 thick line). The dye BHQ10 conjugated to M13 is useful for demonstration of utility but it has a wide bandwidth and is therefore unsuitable for highly multiplexed applications where the signal will overlap with other signals.

Figure 4:
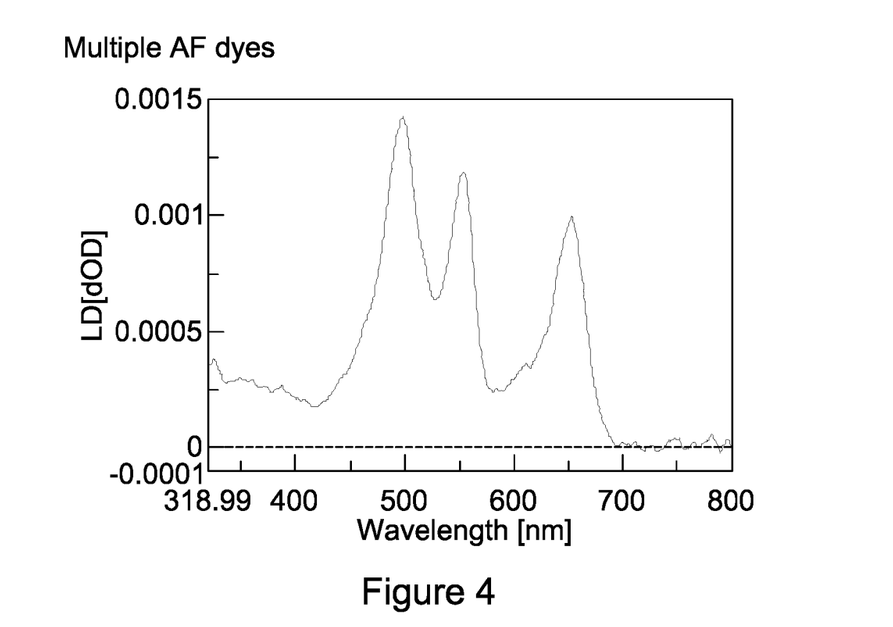
Figure 5:
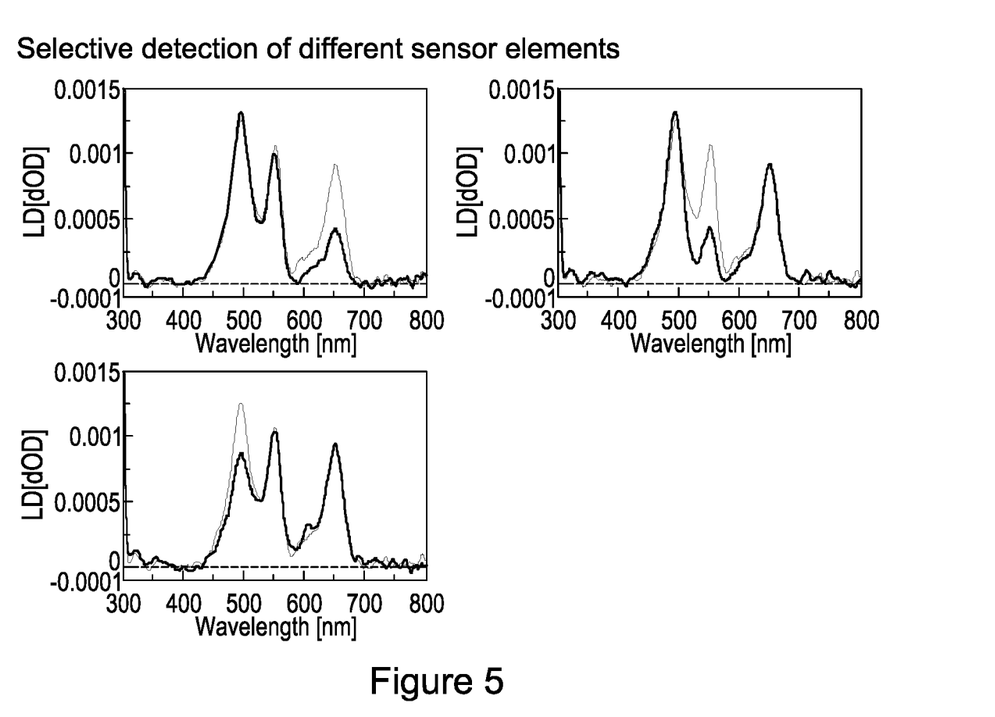
FIG. 5 shows that the change in magnitude of multiple LD signals that result from multiple sensor elements can be detected independently, FIG. 6 demonstrates that the change in response of an LD signal resulting from the change in alignment of a sensor element in response to the presence of a target molecule can be detected independently from a separate sensor element that does not have a receptor for the target molecule, and FIG. 7 demonstrates the change in LD signal produced by two sensors, one having an antibody to *S. typhimurium* (a first target) and the other having an antibody to *E. coli* (a second target), in the absence of bacteria or in the presence of one or both species.
Figure 6:
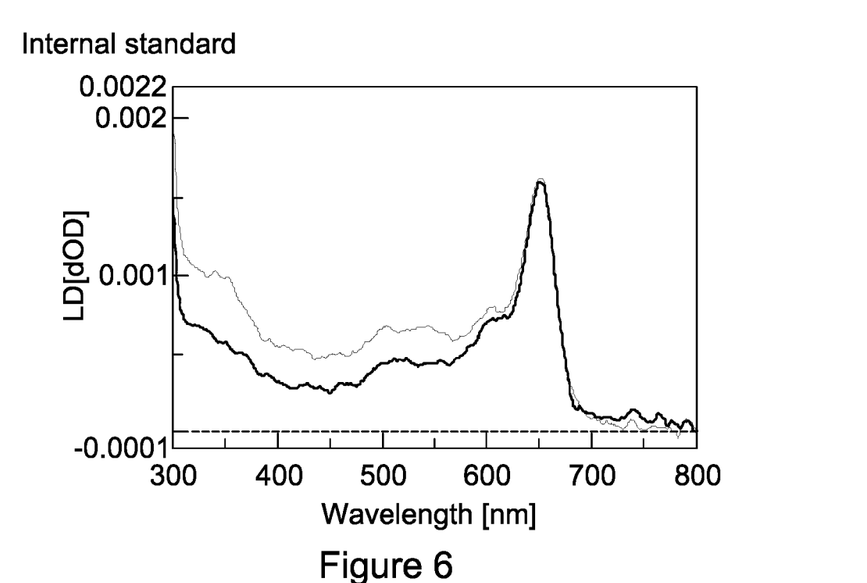

Dyes with much narrower bandwidths are available and have been utilised in this system. For example the AlexaFluor dyes (AF488, AF555 and AF647) conjugated to M13 as shown in FIG. 4. The change in the LD signals resulting from the amounts of these sensor elements can be detected sufficiently independently of the other signals to be useful. A demonstration of this is shown in FIG. 5 where the concentration of each of the three M13-AlexaFluor sensor elements has been reduced separately in three separate measurements.

EXAMPLE

Two types of sensor elements were prepared with the following features:
Sensor 1: M13 bacteriophage with the following attached moieties:
a. AlexaFluor 555 dye
b. An antibody that binds to S. typhimurium bacteria
Sensor 2: M13 bacteriophage with the following attached moieties:
a. AlexaFluor 647 dye
b. An antibody that binds to E. coli bacteria With reference to FIG. 7, the LD signal was measured in the absence of bacteria ("buffer"); in the presence of E. coli ("E. coli O157 10^7 cells/mL"); in the presence of S. typhimurium ("S. typhimurium 10^7 cells/mL"); and in the presence of both E. coli and S. typhimurium ("E. coli O157 10^7 and S. typhimurium 10^7").

Figure 7:
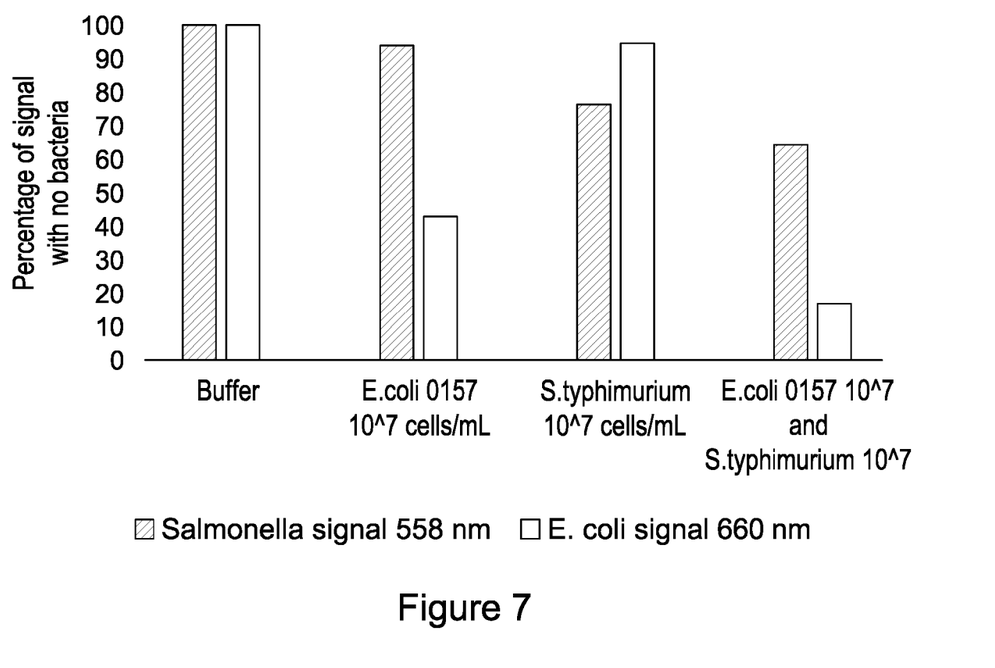

The signal at 558 nm is associated with S. typhimurium detection (hatched lines) and signal at 660 nm is associated with E. coli detection (no fill). In the presence of S. typhimurium the 558 nm signal decreased, in the presence of E. coli the 660 nm signal decreased, and in the presence of both S. typhimurium and E. coli both the 558 nm and the 660 nm signals decreased. This assay provides proof of the utility of the invention in detecting a target which is either present alone in solution or as part of a mixture of targets.

It will be understood that this presents the opportunity to incorporate an internal standard in the measurements whereby the LD signal from a sensor element will decrease in response to the presence of the target molecule (in this case E. coli O157) and an internal standard sensor element that has an LD signal at a different wavelength does not change. This serves to illustrate utility of multiplexed measurements and also the use of an internal standard to correct for any differences in the alignment due to differences in shear flow in an assay system.

It will be understood that the inclusion of other target molecules follows from this methodology whereby the receptor molecule and the chromophore will be different for different target molecules and that these may be measured in the same sample at the same time.

The invention claimed is:
1. A molecular sensor comprising: a flow path configured for flowing a solution potentially containing a target molecule; a source of polarized light; a detector arranged to receive light from the source after it has passed through the flowpath; and a plurality of sensor elements disposed in use in the flow path, each sensor element comprising
(i) a scaffold moiety and (ii) one or more receptor molecules for the target molecule attached to the scaffold moiety to form a scaffold/receptor complex, wherein the scaffold/receptor complex is modified to incorporate a chromophore, wherein the modified scaffold/receptor complex has an aspect ratio greater than 5:1 and wherein the sensor comprises a plurality of distinct groups of sensor elements, the groups having the same scaffold moieties but different chromophores and receptor molecules for different target molecules, such that the dichroic absorbance of each group of sensor elements is at a different wavelength to that of the other groups and each group detects a different target molecule.

2. The molecular sensor according to claim 1 wherein the modified scaffold/receptor complex has an aspect ratio greater than 10:1.

3. The molecular sensor according to claim 1 wherein the scaffold moiety has an aspect ratio greater than 5:1.

4. The molecular sensor according to claim 1, wherein the scaffold moiety is selected from the group consisting of synthetic polymers, carbon nanotubes, biomolecular fibres, crystals, inorganic particles, synthetic biology constructs and mixtures of liquids of different polarities.

5. The molecular sensor according to claim 4 wherein the biomolecular fibre is selected from the group consisting of lipid vesicles, filamentous bacteriophage, polypeptides, proteins and nucleic acid polymers.

6. The molecular sensor according to claim 1 wherein the chromophore is selected from the group consisting of spire compounds, fluoresceins, DNA intercalators, benzopyrones, lanthanide complexes, quantum dots, bodipys black hole quenchers and rhodamines.

7. The molecular sensor according to claim 1 wherein the chromophore is selected from the group consisting of Fluorescamine, Fluorescein-isothiocyanate, N-hydroxysuccinimide-Fluorescein, Rhodamine-isothiocyanate, Tetra-methy 1-rhodamine-isothiocyanate, Eosin-5-maleimide, NBD-chloride and BHQ-10-succinimidyl ester and ethidium bromide.

* * * * *